(12) United States Patent
Piot et al.

(10) Patent No.: US 6,274,131 B1
(45) Date of Patent: Aug. 14, 2001

(54) MASCARA COMPRISING A MIXTURE OF HARD WAXES AND OF FILM-FORMING POLYMER

(75) Inventors: Bertrand Piot, Colombes; Danièle Debert, Savigny sur Orge; Sophie Bodelin-Lecomte, Vanves, all of (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/217,991

(22) Filed: Dec. 22, 1998

Related U.S. Application Data

(63) Continuation-in-part of application No. 09/144,279, filed on Aug. 31, 1998, now abandoned.
(60) Provisional application No. 60/135,117, filed on Aug. 31, 1998.

(30) Foreign Application Priority Data

Dec. 31, 1997 (FR) .................................... 97 16806

(51) Int. Cl.$^7$ .............................. A61K 7/06; A61K 7/032
(52) U.S. Cl. .................... 424/70.7; 424/70.1; 424/70.11; 424/70.12; 424/401
(58) Field of Search .................................. 424/401, 70.7, 424/50.1, 70.11, 70.12

(56) References Cited

U.S. PATENT DOCUMENTS

| | | |
|---|---|---|
| 3,734,874 | 5/1973 | Kibler et al. . |
| 4,233,196 | 11/1980 | Sublett . |
| 4,304,901 | 12/1981 | O'Neill . |
| 4,311,695 | 1/1982 | Starch . |
| 4,871,536 | 10/1989 | Arraudeau et al. . |
| 5,244,497 | 9/1993 | Junino et al. ........................ 106/498 |
| 5,389,363 | 2/1995 | Snyder et al. . |
| 5,534,247 | 7/1996 | Franjac et al. . |
| 5,620,693 | 4/1997 | Piot et al. . |
| 5,747,013 | 5/1998 | Mougin et al. . |
| 5,849,278 | 12/1998 | Piot et al. ........................... 424/70.7 |

FOREIGN PATENT DOCUMENTS

| | | |
|---|---|---|
| 2 123 290 | 2/1984 | (GB) . |
| 8-268841 | 10/1996 | (JP) . |
| WO 96/33690 | 10/1996 | (WO) . |
| WO 96/36323 | 11/1996 | (WO) . |

OTHER PUBLICATIONS

Linda Madore et al., "Water–Soluble Dimethicone Copolyol Waxes for the Personal Care Industry", IFSCC, Oct. 1992, pp. 324–327.
Kirk–Othmer, "Encyclopedia of Chemical Technology", Third Edition, vol. 22, 1979, pp. 333–432.
English Language Derwent Abstract of EP 0 530 084, May 1993.
English Language Derwent Abstract of EP 0 557 196, (Aug. 1993).
English Language Derwent Abstract of EP 0 611 170, (Aug. 1994).
English Language Derwent Abstract of EP 0 639 371, (Feb. 1995).
English Language Derwent Abstract of EP 0 662 312, (Jul. 1995).
English Language Derwent Abstract of EP 0 663 202, (Jul. 1995).
English Language Derwent Abstract of FR 2 528 699, (Dec. 1983).
English Language Derwent Abstract of FR 2 573 305, (May 1986).

*Primary Examiner*—Diana Dudash
*Assistant Examiner*—Gina C Yu
(74) *Attorney, Agent, or Firm*—Finnegan, Henderson, Farabow, Garrett & Dunner, L.L.P.

(57) ABSTRACT

A mascara composition for curling and thickening eyelashes comprising:

a waxes-in-water emulsion of at least one mixture of hard waxes (I), the mixture of waxes (I) containing at least three waxes having melting points ranging from 77° C. to 110° C., the mixture of waxes (I) is present in a content of at least 10% by weight relative to the total weight of the composition, and the mixture of waxes (I) is in the form of particles of at least 1 $\mu$m in size, and at least 0.1% by weight of a polymer system containing at least one film-forming polymer, where the polymer system is capable of forming a film which produces, at a concentration of 7% in water, a greater than 1% retraction of isolated stratum corneum at 30° C. and under a relative humidity of 40%.

27 Claims, No Drawings

MASCARA COMPRISING A MIXTURE OF HARD WAXES AND OF FILM-FORMING POLYMER

This application claims the benefit of U.S. Provisional Application No. 60/135,117 filed Aug. 31, 1998 now ABN, which is a continuation-in-part of U.S. Non-provisional Application 09,144,279 filed Aug. 31, 1998 ABN.

The present invention relates to the use of a mascara composition, comprising a mixture of waxes and of film-forming polymer, for curing and thickening keratin fibers, in particular the eyelashes or the tips of the hair. The invention also relates to a mascara composition comprising a mixture of waxes and a film-forming polymer.

It is common practice to make mascara compositions containing at least one wax. However, this wax is never used alone, since the make-up effect using such compositions proves to be very mediocre, leading to formation of a non-uniform film on the eyelashes, which is reflected in the formation of films that crack immediately after drying.

It is also known, according to patent applications WO 96/36323 and WO 96/33690, to combine a wax and a film-forming polymer in a mascara composition. However, such a combination does not curl the eyelashes well, nor does it give the eyelashes a thick make-up effect.

European patent applications EP-A-557,196 and EP-A-639,371 have also proposed mascara compositions containing microdispersions of waxes combined with film-forming polymers. However, such compositions do not allow a thick make-up effect to be obtained on the eyelashes: such mascaras are thus low-loading.

The aim of the invention is to propose a cosmetic composition which allows improved curling of the eyelashes and eyelashes loaded with make-up product to be obtained. The aim of the invention is also to propose a composition which gives the eyelashes instantaneous, long-lasting curling and which constitutes a makeup product that is well-tolerated by individuals with sensitive eyes.

The inventors have now found, surprisingly, that such a make-up product for the eyelashes can be obtained by using a combination of waxes and of specific film-forming polymers.

Thus, one subject of the invention is the use of a mascara composition for curling and thickening keratin fibers, in particular the eyelashes, comprising:
(i) a waxes-in-water emulsion of at least one mixture of waxes (i), referred to as hard waxes, having a needle penetration ranging from 1 to 7.5 and a melting point ranging from 70° C. to 110° C., the mixture of waxes (I) containing at least one wax (Ia, Ib) having a melting point ranging from 77° C. to 110° C., the mixture of waxes (I) being present in a content of at least 10% by weight relative to the total weight of the composition, the at least one wax being present in the form of particles greater than or equal to at least 1 μm in size, optionally further comprising at least one wax having a melting point ranging from 70° C. to less than 77° C. and having a needle penetration ranging from 1 to 7.5 and being in the form of particles greater than or equal to at least 1 μm in size,
(ii) at least 0.1% by weight, relative to the total weight of the composition, of a polymer system containing a film-forming polymer, the polymer system being capable of forming a film which produces, at a concentration of 7% in water, a greater than I % retraction of isolated stratum corneum at 30° C. and under a relative humidity of 40%.

Another subject of the invention is a method of curling and/or thickening keratin fibers comprising the step of applying to the keratin fibers and effective amount for the curling and/or thickening of a mascara composition comprising:
(i) a waxes-in-water emulsion of a mixture of at least one wax having a needle penetration ranging from 1 to 7.5 and a melting point ranging from 77° C. to 110° C., and at least one wax having a needle penetration ranging from 1 to 7.5 and a melting point ranging from 70° C. to less than 77° C., wherein the mixture is present in an amount of at least 10% by weightr relative to the total weight of said composition, and further wherein the waxes in the mixture are in the form of particle greater than or equal to at leat 1 μm in size, and
(ii) at least 0.1 % by weight, relative to the total weight of the composition, of a polymer system containing at least one film-forming polymer, wherein the polymer system is capable of forming a film which produces, at a concentration of 7% in water, a greater than 1% retraction of isolated stratum corneum at 30° C. and under a relative humidity of 40%.

Another subject of the invention is a mascara composition comprising:
(i) a waxes-in-water emulsion of at least one mixture of waxes (I), referred to as hard waxes, having a needle penetration ranging from 1 to 7.5 and a melting point ranging from 70° C. to 110° C., the mixture of waxes (I) containing at least a first wax (Ia) having a melting point greater than or equal to 77° C. and less than 83° C., a second wax (Ib) having a melting point ranging from 83° C. to 110° C., and a third wax (Ic) having a melting point greater than or equal to 70° C. and less than 77° C., the mixture of waxes (I) being present in a content of at least 10% by weight relative to the total weight of the composition, the mixture of waxes (I) being in the form of particles greater than or equal to at least 1 μm in size,
(ii) at least 0.1% by weight, relative to the total weight of the composition, of a polymer system containing a film-forming polymer, the said polymer system being capable of forming a film which produces, at a concentration of 7% in water, a greater than 1% retraction of isolated stratum corneum at 30° C. and under a relative humidity of 40%.

Another subject of the invention is a mascara product comprising a reservoir containing a mascara composition as defined above, and equipped with a system for applying the composition to keratin fibers, in particular the eyelashes.

Another subject of the invention is a process for making up keratin fibers, in particular the eyelashes, which involves applying a composition as defined above to the keratin fibers.

According to the invention, the waxes are in the form of particles preferably having a size greater than or equal to 1.5 μm, in particular ranging from 1.5 to 10 μm, and better still ranging from 1.5 μm to 3.5 μm.

The term hard wax (or wax (I)) is understood to refer to a wax having a melting point ranging from 70° C. to 110° C. and a needle penetration ranging from 1 to 7.5. The needle penetration of waxes is determined according to French standard NF T 60-123 or US standard ASTM D 1321, at a temperature of 25° C. According to these standards, the needle penetration is a measurement of the depth, expressed in tenths of a millimeter, to which a standardized needle weighing 2.5 g, located in a movable mounting weighing 97.5 g and placed on the wax to be tested, for 5 seconds, penetrates into the wax.

The waxes (I) used in accordance with the invention can be selected from waxes of animal origin, waxes of plant origin, waxes of mineral origin, synthetic waxes and the various fractions of waxes of natural origin, all of these waxes having the two characteristics (needle penetration, melting point) mentioned above.

The waxes (I) can be selected in particular from rice bran wax, carnauba wax, ouricurry wax, candelilla wax, montan waxes, sugar cane waxes, and certain polyethylene waxes which satisfy the criteria for the waxes (I).

Advantageously, the composition according to the invention can comprise an amount of the mixture of waxes (I) preferably ranging from 10% to 30% by weight, relative to the total weight of the composition, more preferably from 13% to 25% and better still at least 15%, and especially from 15% to 20%.

The mixture of waxes (I) can comprise at least a first wax (Ia) having a melting point of greater than or equal to 77° C. and less than 83° C. Such a wax can be, for example, rice bran wax.

The mixture of waxes (I) can also comprise at least a second wax (Ib) having a melting point ranging from 83° C. to 110° C. This second wax (Ib) can be used alone in the mixture of waxes (I) or can be combined with the wax (Ia). Such a wax (Ib) can be, for example, carnauba wax, ouricurry wax or montan waxes. Carnauba wax is preferably used.

The mixture of waxes (I) can also comprise a third wax (Ic) having a melting point of greater than or equal to 70° C. and less than 77° C. Such a wax can be, for example, candelilla wax.

For the use according to the invention, the mascara composition preferably comprises a mixture of waxes (I) containing at least a first wax (Ia) and at least a second wax (Ib) as defined above.

The mixture of waxes (I) can comprise from 35% to 65% by weight of wax (Ia), relative to the total weight of the mixture of waxes (I), and from 65% to 35% by weight of wax (Ib).

Preferably, the mixture of waxes (I) can comprise, in addition to the first and second waxes (Ia, Ib), a third wax (Ic) as defined above. This third wax is preferably present in the composition in a content ranging from 5% to 20% by weight, relative to the total weight of the mixture of waxes (I).

Advantageously, the first, second and third waxes (Ia, Ib, Ic) can be present in the composition in a weight ratio (weight/total weight of waxes (I)) ranging, respectively, from:

wax (Ia): 0.35 to 0.5,
wax (Ib) : 0.35 to 0.5,
wax (Ic): 0.05 to 0.2.

For the use according to the invention, the composition comprises, in addition to the mixture of wax (I), at least one polymer system capable of forming a film which produces, at a concentration of 7% in water, preferably a greater than 1%, more preferably greater than 1.2% and better still greater than 1.5%, retraction of isolated stratum corneum, at 30° C. and under a relative humidity of 40%. Such polymers give very good curling of the eyelashes.

Method for measuring retraction

The principle consists in measuring, before and after treatment, the length of a test sample of isolated stratum corneum and in determining the percentage of retraction of the test sample.

1 cm×0.4 cm test samples of stratum corneum ranging from 10 to 20 $\mu$m in thickness, arranged on an MTT 610 extensiometer sold by the company Diastron, are used.

The test sample is placed between 2 jaws and then left for 12 hours in an atmosphere at 30° C. and 40% relative humidity.

The test sample is stretched, at a speed of 2 mm/minute, to an elongation of between 5 and 10% of the initial length in order to determine the length $I_1$ at which the test sample begins to exert a force on the jaws which is detected by the machine.

The test sample is then relaxed and 2 mg of an aqueous composition containing 7% by weight of polymer is applied to the stratum corneum. After total evaporation of the composition, the test sample is stretched under the same conditions as those described above in order also to determine the length $I_1$ for the treated test sample.

The percentage of retraction is determined by the equation: $100 \times (I_2 - I_1)/I_1$.

The term "polymer system" is understood to refer either to a polymer alone or to a polymer combined with at least one other polymer or to a polymer combined with at least one plasticizer, so as to obtain the desired mechanical properties.

The expression "capable of forming a film" is understood to refer to a polymer system which allows a film to be formed: when it is spread on glass, the polymer system must dry without cracking.

The film-forming polymer of the polymer system according to the invention can be a polymer of natural origin or a synthetic polymer. The film-forming polymer can especially be a water-soluble or water-dispersible polymer.

The expression polymer of natural origin is understood to refer to polymers of plant origin and of animal origin.

As polymers of plant origin, mention may be made in particular of proteins and protein hydrolysates, and more particularly extracts of cereals, of leguminous plants and of oleaginous plants, such as extracts of wheat, of corn, of rye, of *Triticum aestivum* wheat, of buckwheat, of sesame, of *Triticum spelta*, of pea, of bean, of lentil, of soybean and of lupin.

As polymer of animal origin, use may be made of polymers obtained from the carapace of insects or crustaceans. Mention may be made, for example, of chitin and its derivatives, in particular chitosan which is a deacetyl derivative of chitin, as well as chitosan derivatives such as hydroxypropylchitosan, the succinyl derivative of chitosan, chitosan lactate, chitosan glutamate and carboxymethyl chitosan succinamide.

The polymers of natural origin, which are optionally modified, can be selected for example from shellac resin, sandarac gum, dammar resins, elemi gums, copal resins and cellulose derivatives.

As suitable water-soluble polymers of natural origin, mention may be made of the hydroxypropylchitosan sold under the name "HPCH powder" by the company Ichimaru Pharcos and the wheat protein hydrolysate sold under the name "Tritisol" by the company Croda (having a molecular weight of about 250,000 daltons).

The synthetic polymers can be of polycondensate type or of radical type.

As polycondensates, mention may be made of anionic, cationic, nonionic or amphoteric polyurethanes, polyurethane-acrylics, polyurethane-polyvinylpyrrolidones, polyester-polyurethanes, polyether-polyurethanes, polyurea-urethanes, polyureas, sulphopolyesters (which are described in particular in patents U.S. Pat. No. 3,734,874, U.S. Pat. No. 4,233,196 and U.S. Pat. No. 4,304,901, the disclosures of which are specifically incorporated by reference herein) and mixtures thereof.

As radical polymers, mention may be made of acrylic polymers, acrylic/styrene copolymers and vinyl copolymers such as vinyl ester copolymers.

As suitable synthetic polymer, mention may be made in particular of the polyester-polyurethane dispersions sold under the names "SANCURE 2060" (polyester-polyurethane), "SANCURE 815" (polyester-polyurethane) or alternatively sulphopolyesters based on isophthalate/sulphoisophthalate, and more particularly the sulphopolyesters obtained by condensation of di-ethylene glycol, cyclohexanedi-methanol, isophthalic acid and sulphoisophthalic acid, in particular those sold under the name AQ55S by the company Eastman.

When the film-forming polymer does not by itself allow a film having the characteristics mentioned above to be obtained, it is possible to add a compound whose function is to modify the properties of the film-forming polymer in order to obtain the desired polymer system. Thus, according to one embodiment of the composition according to the invention, the said polymer system can comprise at least one film-formation auxiliary agent which makes it possible to obtain a film having the characteristics as described above. The film-formation auxiliary agent makes it possible in particular to obtain a film which allows good curling of the eyelashes to be obtained. In this case, the polymer system comprises a mixture of one or more film-forming polymers and at least one film-formation auxiliary agent.

Such a film-formation auxiliary agent can be selected from any compound known to those skilled in the art as being capable of fulfilling the desired function, and can be selected in particular from plasticizers. In addition, when the polymer system according to the invention comprises at least one aqueous dispersion of particles of film-forming polymer, the film-formation auxiliary agent can also be selected from coalescence agents. This auxiliary agent can be water-soluble or water-insoluble and can optionally be in the form of an aqueous dispersion.

In particular, mention may be made, alone or as a mixture, of the common plasticizers or coalescence agents, such as:

glycols and their derivatives, such as diethylene glycol ethyl ether, diethylene glycol methyl ether, diethylene glycol butyl ether, diethylene glycol hexyl ether, ethylene glycol ethyl ether, ethylene glycol butyl ether or ethylene glycol hexyl ether;

glycerol esters, propylene glycol derivatives and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether and propylene glycol butyl ether, acid esters, in particular carboxylic acid esters, such as citrates, phthalates, adipates, carbonates, tartrates, phosphates and sebacates, oxyethylenated derivatives such as oxyethylenated oils, in particular plant oils such as castor oil; silicone oils, water-soluble polymers having a low glass transition temperature, of less than 25° C., preferably less than 15° C.

The amount of film-formation auxiliary agent can be selected by a person skilled in the art on the basis of his or her general knowledge, so as to obtain a polymer system which leads to a film having the desired mechanical properties, while at the same time retaining acceptable cosmetic properties for the composition.

The composition can preferably comprise from 0.1% to 10% by weight, more preferably from 0.3% to 7%, of film-forming polymer solids relative to the total weight of the composition.

The polymer system used (polymer(s) or polymer and plasticizer) according to the invention can be present in particular in an active material (A.M.) amount preferably ranging from 0.1 to 15%, and better still from 0.3 to 10%, of the total weight of the composition.

In addition, the composition for the use according to the invention can comprise at least one wax (II), referred to as soft wax, having a melting point of greater than or equal to 50° C. and less than 70° C., and a needle penetration of greater than 7.5, and preferably less than or equal to 217, measured according to the conditions defined above for the waxes (I). This wax (II) makes it possible in particular to impart flexibility to the make-up applied to the eyelashes.

These waxes (II) can be selected in particular from beeswax, lanolin waxes, paraffin waxes, ceresin waxes, microcrystalline waxes, ozocerites, spermacetis, certain polyethylene waxes with a molecular weight such that they satisfy the criteria of the waxes (II), and hydrogenated plant oils.

Among the hydrogenated plant oils, mention may be made of hydrogenated jojoba waxes and hydrogenated oils which are obtained by catalytic hydrogenation of fatty substances composed of a linear or non-linear $C_8$–$C_{32}$ fatty chain and which have the qualities corresponding to the definition of waxes. Mention may be made in particular of hydrogenated sunflower oil, hydrogenated castor oil, hydrogenated coconut oil and hydrogenated lanolin.

Advantageously, the waxes (I) and the waxes (II) are present in the composition in a waxes (I)/wax (II) weight ratio which can range preferably from 2 to 5 and more preferably from 2.5 to 3.5.

The composition for the use according to the invention can contain emulsifying surfactants present in a proportion preferably ranging from 2 to 30% by weight relative to the total weight of the composition, and better still from 5% to 20%. These surfactants can be selected from anionic or nonionic surfactants. Reference may be made to the document "Encyclopedia of Chemical Technology, Kirk-Othmer", Volume 22, pp. 333–432, 3rd Edition, 1979, Wiley, for the definition of the properties and functions (emulsifying) of surfactants, in particular pp. 347–377 of this reference which is hereby specifically incorporated by reference, for the anionic and nonionic surfactants.

The surfactants preferably used in the compositions according to the invention are:

among the nonionic surfactants: fatty acids, fatty alcohols, polyethoxylated or polyglycerolated fatty alcohols such as polyethoxylated stearyl or cetylstearyl alcohols, fatty acid esters of sucrose, alkylglucose esters, in particular polyoxyethylenated fatty esters of ($C_1$–$C_6$) alkylglucose, among the anionic surfactants: $C_{16}$–$C_{30}$ fatty acids neutralized with amines, ammonia or alkaline salts.

Surfactants which allow an oil-in-water emulsion to be obtained are preferably used.

In the composition according to the invention, the water can advantageously represent from 30 to 80% by weight of the total weight of the composition.

In addition, the composition can comprise at least one thickener, preferably of hydrophilic nature. This can be selected, for example, from carboxyvinyl polymers (carbomer), acrylic copolymers such as acrylate/alkylacrylate copolymers, polyacrylamides, polysaccharides, natural gums and clays.

The composition can advantageously comprise a silicone surfactant having an HLB ranging from 8 to 16. Preferably, such a surfactant is a dimethicone copolyol. When the composition according to the invention is applied to the eyelashes, the silicone surfactant allows better staying power over time and better resistance to the mechanical stresses of the composition thus applied.

The dimethicone copolyols can be selected from the compounds of the general formula (I):

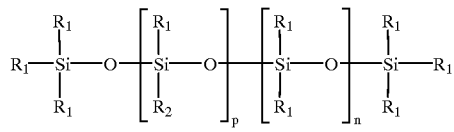

(I)

in which formula:

R$_1$ independently represent a hydrogen atom, a linear or branched C$_1$–C$_{30}$ alkyl radical or a phenyl radical, R$_2$ independently represent —(C$_x$H$_{2x}$)—(OC$_2$H$_4$)$_a$—(OC$_3$H$_6$)$_b$—OR$_3$, R$_3$ are independently selected from a hydrogen atom, a linear or branched alkyl radical having from 1 to 12 carbon atoms and a linear or branched acyl radical having from 2 to 12 carbon atoms, n ranges from 0 to 1000, p ranges from 1 to 30, a ranges from 0 to 50, b ranges from 0 to 50, a+b is greater than or equal to 1, x ranges from 1 to 5, the number-average molecular weight is greater than or equal to 15,000 and preferably ranges from 25,000 to 75,000.

Preferably, oxyalkylenated silicones of general formula (I) which satisfy at least one, and more preferably all, of the conditions below are used:

R$_1$ denotes a methyl radical,

R$_3$ represents a hydrogen atom, a methyl radical or an acetyl radical, and preferably hydrogen, p ranges from 8 to 20, a ranges from 5 to 40 and preferably from 15 to 30, b ranges from 5 to 40 and preferably from 15 to 30, x is equal to 2 or 3, n ranges from 20 to 600, preferably from 50 to 500 and even more particularly from 100 to 300.

Such silicones are described, for example, in U.S. Pat. No. 4,311,695 which is hereby specifically incorporated by reference.

Dimethicone copolyols were presented in particular by the company Dow Corning during the 17th international congress of the I.F.S.C.C. of October 1992 and reported in the article "Water-soluble dimethicone copolyol waxes for personal care industry" by Linda Madore et al., pages 1 to 3, the disclosure of which is hereby specifically incorporated by reference.

These dimethicone copolyols are water-soluble polydimethylsiloxanes (PDMS) containing one or more ether functions (oxyalkylene, in particular oxyethylene and/or oxypropylene). Such dimethicone copolyols are sold in particular by the company Goldschmidt under the name ABIL B8851 or ABIL B88183. Mention may also be made of the compounds KF 351 to 354 and KF 615 A sold by the company Shin Etsu or DMC 6038 from the company Wacker.

The dimethicone copolyol derivatives which can be used may be, in particular, dimethicone copolyols containing a phosphate, sulphate, myristamide propyldimethylammonium chloride, stearate, amine, glycomodified, etc. group. The compounds sold by the company Siltech under the name SILPHOS A100, SILTECH AMINE 65, SILWAX WDIS and myristamido silicone quat, or by the company Phoenix under the name PECOSIL PS 100, can be used in particular as dimethicone copolyol derivatives.

The derivatives sold by the company Wacker under the name VP 1661, or by the company Dow Corning under the name 2501 cosmetic wax, can also be used.

The silicones most particularly preferred are, for example, those sold by the company Dow Corning under the trade name Q2-5220 and by the company Rhône Poulenc under the name MIRASIL DMCO.

The composition according to the invention can also contain ingredients commonly used in cosmetics, such as vitamins, trace elements, softeners, sequestering agents, fragrances, oils, silicones and cohesion agents, as well as the acidifying or basifying agents usually used in the cosmetics field, fillers, pigments and emollients, usually used in amounts ranging from 1 to 10%; preserving agents.

The composition according to the invention is intended for a mascara product comprising a reservoir, containing the said mascara composition, and a system for applying the said composition to keratin fibers, in particular the eyelashes. The reservoir is equipped, in a known manner, with an opening in which is housed a draining system. The application system contains a stem which is fitted, at a first end, with a brush, and, at a second end, with a stopper intended to close the reservoir. Such packaging is illustrated in particular in FIG. 7 of patent application EP-A-611,170 the disclosure of which is specifically incorporated herein by reference.

The invention is illustrated in greater detail, but in no way limited by, the examples which follow.

EXAMPLE 1

A mascara having the following composition was prepared:

| | | |
|---|---|---|
| rice bran wax | | 7 g |
| carnauba wax | | 7 g |
| candelilla wax | | 2.8 g |
| triethanolamine stearate | | 8.4 g |
| beeswax | | 6 g |
| wheat protein hydrolysate sold under the name "TRITISOL" by the company Croda | | 0.31 g AM |
| hydroxyethylcellulose | | 1.5 g |
| pigments | | 8 g |
| preserving agents | qs | |
| water | qs | 100 g |

The waxes, the surfactant and the preserving agents were melted and mixed together at 90° C. The pigments were dispersed in the molten mixture at 90° C. The TRITISOL and the hydroxyethylcellulose were dissolved in the cold water. The aqueous phase was then heated to 90° C. and poured into the molten mixture with stirring, while maintaining the temperature at about 90° C. until the mixture was homogeneous. Next, the composition was cooled to room temperature.

A mascara in the form of a waxes-in-water dispersion in which the wax particles are greater than 1.5 μm in size was thus obtained.

By applying the mascara to the eyelashes, it was found that they curled very well and were well laden with make-up: the eyelashes have a good thickness of make-up.

EXAMPLE 2

A mascara having the following composition was prepared:

| | | |
|---|---|---|
| rice bran wax | | 10 g |
| carnauba wax | | 8 g |
| candelilla wax | | 1 g |
| triethanolamine stearate | | 9 g |
| beeswax | | 4 g |
| wheat protein hydrolysate sold under the name "TRITISOL" by the company Croda | | 0.4 g AM |
| hydroxyethylcellulose | | 1.5 g |
| pigments | | 5 g |
| preserving agents | | qs |
| water | qs | 100 g |
| dimethicone copolyol sold under the name "Q2-5520" by the company Dow Corning | | 0.3 g |

A mascara which imparts good curling to the eyelashes after it has been applied was thus obtained. The make-up applied to the eyelashes was thick and had good staying power over time.

EXAMPLE 3

A mascara having the following composition was prepared:

| | | |
|---|---|---|
| rice bran wax | | 8 g |
| carnauba wax | | 8 g |
| paraffin wax | | 2 g |
| triethanolamine stearate | | 9 g |
| beeswax | | 3 g |
| copolymer of diglycol/cyclohexanedimethanol/ isophthalates/sulphoisophthalates sold under the name "EASTMAN AQ-55S" by the company Eastman | | 1 g |
| hydroxyethylcellulose | | 1.2 g |
| pigments | | 7 g |
| preserving agents | qs | |
| water | qs | 100 g |

After applying this mascara to the eyelashes, good curling of the eyelashes was found, as well as a thick make-up applied to the eyelashes.

EXAMPLE 4: (INVENTION)

A mascara having the following composition was prepared:

| | | |
|---|---|---|
| carnauba wax | | 20.1 g |
| polyoxyethylenated (30 EO) glyceryl monostearate (TAGAT S from the company Goldschmidt) | | 6.71 g |
| hydroxyethylcellulose (Cellosize QP4400M from the company Amerchol) | | 1 g |
| gum arabic | | 1.5 g |
| panthenol | | 1 g |
| pigment | | 5 g |
| sodium hydroxide | qs pH 7 | |
| preserving agent | qs | |
| water | qs | 100 g |

EXAMPLE 5: (COMPARATIVE)

A wax microdispersion, as described in patent application EP-A-557,196, having the following composition was prepared:

| | | |
|---|---|---|
| carnauba wax | | 22.5 g |
| TAGAT S | | 7.5 g |
| preserving agent | qs | |
| water | qs | 100 g |

The wax microdispersion has an average wax particle size of 283 nm.

Next, a mascara having the composition below was prepared, using the wax microdispersion:

| | | |
|---|---|---|
| wax microdispersion | | 89.5 g |
| hydroxyethylcellulose (CELLOSIZE QP4400M from the company Amerchol) | | 1 g |
| gum arabic | | 1.5 g |
| panthenol | | 1 g |
| pigment | | 5 g |
| sodium hydroxide | qs pH 7 | |
| preserving agent | qs | |
| water | qs | 100 g |

Eyelashes were made up using the compositions of Examples 4 and 5 and the make-up results obtained were compared: it was found that only the eyelashes made up with the composition of Example 4 (invention) had a thick and curling make-up effect.

EXAMPLES 6 TO 9:

3 mascaras according to the invention (Examples 6 to 8) and a mascara not forming part of the invention (Example 9) having the following composition were prepared:

| | Example 6 (invention) | Example 7 (invention) | Example 8 (invention) | Example 9 (outside the invention) |
|---|---|---|---|---|
| carnauba wax | 20.1 g | 8.375 g | 8.375 g | 9 g |
| beeswax | — | — | — | 11.1 g |
| rice bran wax | — | 8.375 g | 8.375 g | — |
| candelilla wax | — | 3.35 g | 3.35 g | — |
| stearic acid | 4.65 g | 4.65 g | 4.65 g | 4.65 g |
| triethanolamine | 2.05 g | 2.05 g | 2.05 g | 2.05 g |
| water | qs 100 g | qs 100 g | qs 100 g | qs 100 g |
| preserving agent | 0.3 g | 0.3 g | 0.3 g | 0.3 g |
| black iron oxide | 5 g | 5 g | 5 g | 5 g |
| hydroxyethylcellulose (Cellosize QP4400M from Amerchol) | 1 g | 1 g | 0.7 g | 1 g |
| gum arabic | 1.5 g | 1.5 g | 1.5 g | 1.5 g |
| Tritisol wheat protein hydrolysate | — | — | 0.3 g AM | — |
| panthenol | 1 g | 1 g | 1 g | 1 g |
| TOTAL | 100 g | 100 g | 100 g | 100 g |

Eyelashes were made up using the compositions of Examples 6 to 9 and the make-up results obtained were compared: it was found that the eyelashes made up with the compositions of Examples 6 to 8 (invention) had a thicker and more curling make-up effect than that obtained with the composition of Example 9 (which does not form part of the invention).

We claim:

1. A mascara composition comprising:
   (i) waxes-in-water emulsion of a mixture of waxes having a needle penetration ranging from 1 to 7.5 and a melting point ranging from 70° C. to 110° C., wherein said mixture of waxes comprises at least one first wax having said needle penetration and a melting point of at least 77° C. and less than 83° C., at least one second wax having said needle penetration and a melting point ranging from 83° C. to 110° C., and at least one third wax having said needle penetration and a melting point of at least 70° C. and less than 77° C., wherein said mixture of waxes is present in an amount of at least 10% by weight relative to the total weight of said composition, and said mixture of waxes is in the form of particles of at least 1.0 µm in size, and
   (ii) at least 0.1% by weight, relative to the total weight of said composition, of a polymer system containing at least one film-forming polymer, wherein said polymer system is capable of forming a film which produces, at a concentration of 7% in water, a greater than 1% retraction of isolated stratum corneum at 30° C. and under a relative humidity of 40%.

2. A composition according to claim 1, wherein said at least one first wax is a rice bran wax.

3. A composition according to claim 1, wherein said at least one second wax is selected from carnauba wax, ouricurry wax, and montan waxes.

4. A composition according to claim 3 wherein said at least one second wax is carnauba wax.

5. A composition according to claim 1, wherein said at least one third wax is candelilla wax.

6. A composition according to claim 1, wherein said mixture of waxes comprises at least 15% by weight, relative to the total weight of said composition.

7. A composition according to claim 1, wherein said first, second, and third waxes are present in a weight ratio to the total weight of wax of:
   said first wax 0.35:1 to 0.5:1,
   said second wax 0.35:1 to 0.5:1,
   said third wax 0.05:1 to 0.2:1.

8. A composition according to claim 1, wherein said first, second, and third waxes are particles of at least 1.5 µm in size.

9. A composition according to claim 1, wherein said at least one film-forming polymer is selected from polymers of plant origin, polymers of animal origin, radical polymers and polycondensates.

10. A composition according to claim 1, wherein said at least one film-forming polymer is a water-soluble or water-dispersible polymer.

11. A composition according to claim 1, wherein said at least one film-forming polymer is selected from proteins, protein hydrolysates, chitin and its derivatives, shellac resin, sandarac gum, dammar resins, elemi gums, copal resins, cellulose derivatives, polycondensates and radical synthetic polymers.

12. A composition according to claim 1, wherein said at least one film-forming polymer is selected from proteins, protein hydrolysates, chitin and its derivatives, polyesters-polyurethanes, and sulphopolyesters.

13. A composition according to claim 1, wherein said at least one film-forming polymer is selected from hydroxypropylchitosan and wheat protein hydrolysate.

14. A composition according to claim 1, wherein said water-soluble polymer is wheat protein hydrolysate.

15. A composition according to claim 11, wherein said polycondensates are selected from polyester-polyurethanes and sulphopolyesters.

16. A composition according to claim 1, wherein said waxes-in-water emulsion further comprises at least one wax having a melting point of at least 50° C. and less than 70° C. and a needle penetration of greater than 7.5.

17. A composition according to claim 1, wherein said waxes-in-water emulsion further comprises at least one wax having a melting point of at least 50° C. and less than 70° C. and a needle penetration of greater than 7.5 and less than or equal to 217.

18. A composition according to claim 1, wherein the weight ratio of said at least one first wax, at least one second wax, and at least one third wax to said at least one wax having a melting point of at least 50° C. and less than 70° C. and a needle penetration of greater than 7.5 ranges from 2:1 to 5:1.

19. A composition according to claim 1, wherein said ratio ranges from 2.5:1 to 3.5:1.

20. A composition according to claim 1, wherein said mascara composition further comprises at least one thickener.

21. A composition according to claim 1, wherein said mascara composition comprises at least one silicone surfactant having an HLB ranging from 8 to 16.

22. A composition according to claim 21, wherein said at least one silicone surfactant is a dimethicone copolyol.

23. A mascara product comprising a reservoir containing a mascara composition according to claim 1, and a system for applying said composition to keratin fibers.

24. A process for making up keratin fibers comprising the step of applying an effective amount of at least one mascara composition according to claim 1 to said keratin fibers.

25. A process according to claim 24, wherein said keratin fibers are eyelashes.

26. A method of curling and/or thickening keratin fibers comprising the step of applying to said keratin fibers an effective amount for said curling and/or thickening of a mascara composition comprising:
   (i) a waxes-in-water emulsion of a mixture of waxes having a needle penetration ranging from 1 to 7.5 and a melting point ranging from 70° C. to 110° C., wherein said mixture of waxes comprises at least one first wax having said needle penetration and a melting point of at least 77° C. and less than 83° C., at least one second wax having said needle penetration and a melting point ranging from 83° C. to 110° C., and at least one third wax having said needle penetration and a melting point of at least 70° C. and less than 77° C.,
   wherein said mixture of waxes is present in an amount of at least 10% by weight relative to the total weight of said composition, and said mixture of waxes is in the form of particles of at least 1.0 µm in size, and
   (ii) at least 0.1% by weight, relative to the total weight of said composition, of a polymer system containing at least one film-forming polymer, wherein said polymer system is capable of forming a film which produces, at a concentration of 7% in water, a greater than 1% retraction of isolated stratum corneum at 30° C. and under a relative humidity of 40%.

27. A method according to claim 26, wherein said mixture of waxes has a particle size of greater than or equal to 1.5 µm.

* * * * *

UNITED STATES PATENT AND TRADEMARK OFFICE
CERTIFICATE OF CORRECTION

PATENT NO.   : 6,274,131 B1
DATED        : August 14, 2001
INVENTOR(S)  : Piot et al.

Page 1 of 1

It is certified that error appears in the above-identified patent and that said Letters Patent is hereby corrected as shown below:

<u>Title page,</u>
Item [57], ABSTRACT, line 5, replace "77" with -- 70 --; and <u>Column 1,</u>
Lines 5-10, replace the current claim for priority with -- This application claims the benefit of U.S. Provisional Application No. 60/135,117, filed August 31, 1998, now abandoned, which originated from the conversion to a provisional application of U.S. Nonprovisional Application No. 09/144,279, filed August 31, 1998. --.

Signed and Sealed this

Thirtieth Day of April, 2002

Attest:

Attesting Officer

JAMES E. ROGAN
*Director of the United States Patent and Trademark Office*